United States Patent
Zhu et al.

(10) Patent No.: US 12,048,317 B2
(45) Date of Patent: Jul. 30, 2024

(54) ASTAXANTHIN-CONTAINING CONDIMENT AND A PREPARATION METHOD THEREFOR

(71) Applicant: South China University of Technology, Guangzhou (CN)

(72) Inventors: Mingjun Zhu, Guangzhou (CN); Li Chen, Guangzhou (CN)

(73) Assignee: South China University of Technology, Guangzhou (CN)

( * ) Notice: Subject to any disclaimer, the term of this patent is extended or adjusted under 35 U.S.C. 154(b) by 846 days.

(21) Appl. No.: 17/043,863

(22) PCT Filed: Oct. 22, 2018

(86) PCT No.: PCT/CN2018/111208
§ 371 (c)(1),
(2) Date: Sep. 30, 2020

(87) PCT Pub. No.: WO2019/196374
PCT Pub. Date: Oct. 17, 2019

(65) Prior Publication Data
US 2021/0137144 A1    May 13, 2021

(30) Foreign Application Priority Data

Apr. 11, 2018 (CN) .......................... 201810322202.6

(51) Int. Cl.
| | | |
|---|---|---|
| *A23L 27/10* | (2016.01) | |
| *A23L 27/00* | (2016.01) | |
| *A23L 29/212* | (2016.01) | |
| *A23L 29/281* | (2016.01) | |
| *A23L 31/15* | (2016.01) | |
| *A23L 33/145* | (2016.01) | |
| *A23P 10/30* | (2016.01) | |
| *A61K 9/48* | (2006.01) | |
| *A61K 9/50* | (2006.01) | |
| *A61K 31/122* | (2006.01) | |
| *C12N 1/06* | (2006.01) | |

(52) U.S. Cl.
CPC .............. *A23L 27/10* (2016.08); *A23L 27/72* (2016.08); *A23L 29/212* (2016.08); *A23L 29/284* (2016.08); *A23L 31/15* (2016.08); *A23L 33/145* (2016.08); *A23P 10/30* (2016.08); *A61K 9/4833* (2013.01); *A61K 9/5036* (2013.01); *A61K 31/122* (2013.01); *C12N 1/063* (2013.01); *A23V 2002/00* (2013.01)

(58) Field of Classification Search
CPC ........ A23L 27/10; A23L 27/72; A23L 33/145; A23L 29/212; A23L 31/15; A23L 29/284; A23P 10/30; C12N 1/063
See application file for complete search history.

(56) References Cited

FOREIGN PATENT DOCUMENTS

| CN | 1748573 A | 3/2006 |
|---|---|---|
| CN | 105348165 A | 2/2016 |

OTHER PUBLICATIONS

English translation of WO 2010/087373 (Year: 2010).*
English translation of CN105348165 (Year: 2015).*
Search Report dated Jan. 29, 2019, Application No. PCT/CN2018/111208.

* cited by examiner

*Primary Examiner* — Katherine D Leblanc
(74) *Attorney, Agent, or Firm* — The Dobrusin Law Firm, P.C.; Eric Kurtycz

(57) ABSTRACT

The present invention belongs to the technical field of condiment preparation, and specifically relates to an astaxanthin-containing condiment and a preparation method therefor. In this method, first a low-speed bead milling method is used to break the cell wall of the yeast, such that astaxanthin is directly emulsified in water, and the concentration of astaxanthin can reach 1043.17 mg/L, avoiding the use of emulsifiers and organic solvents; then a small amount of Angel yeast compound enzyme is added for enzymolysis, with the yield of amino nitrogen as high as 3.51% to 3.65% and the yield of solid matter as high as 47.18% to 49.22%; and finally the gelatinized porous starch solution and gelatin are sequentially added, with the encapsulation rate and drug-loading rate of the obtained astaxanthin-containing microcapsule powder being 75.62% to 88.5% and 1.55-10.42 mg/g, respectively. The microcapsule powder has bright color, and high astaxanthin stability and water solubility. The preparation method has the advantages of short time and mild conditions, which can reduce the industrial application cost of *Phaffia rhodozyma*.

9 Claims, No Drawings

ASTAXANTHIN-CONTAINING CONDIMENT AND A PREPARATION METHOD THEREFOR

FIELD OF THE INVENTION

The present invention belongs to the technical field of condiment preparation, and specifically relates to an astaxanthin-containing condiment and a preparation method therefor.

BACKGROUND OF THE INVENTION

Yeast extract contains peptide compounds, 18 kinds of amino acids, various nucleotides, sugars and various trace elements needed by the human body. It is a natural compound additive with three functions of flavoring, nutrition and health care. It is prepared by using yeast as the raw material and using modern biotechnology to degrade the protein and nucleic acid substances in the yeast. Among the yeast raw materials used, *P. rhodozyma* has a total nitrogen content of 4.8%, a total carbon content of 40%, and an average RNA content of 8.2%, and is a preferred raw material for yeast extract. Compared with other yeasts, *P. rhodozyma* cells are rich in astaxanthin, which is one of the sources of natural astaxanthin. Therefore, the yeast extract prepared from *P. rhodozyma* also has the antioxidant and immune enhancing effects of astaxanthin.

In order to obtain the intracellular product astaxanthin of *P. rhodozyma*, a simple and efficient cell-wall breaking method must be established in the process of industrial development. Glass bead milling is a simple, effective and suitable method for large-scale applications. However, high-speed bead mills are often used in the prior art to improve wall-breaking efficiency, which will generate local high temperature and cause astaxanthin loss. Besides, since astaxanthin is insoluble in water and most organic solvents, acetone and ethanol are currently often used in extraction and purification, which will lead to presence of acetone residue and large consumption of ethanol.

In addition, astaxanthin has long conjugated double bonds and hydroxy ketones at the end of the molecule, and is thus instable due to these highly unsaturated structures; therefore, astaxanthin is microencapsulated in order to improve its stability and its sustained-release effect during use. However, a single wall material is often used in existing studies, difficult to significantly improve the stability of astaxanthin.

CONTENTS OF THE INVENTION

In order to overcome the shortcomings and deficiencies of the prior art, the primary object of the present invention is to provide a method for preparing an astaxanthin-containing condiment.

Another object of the present invention is to provide an astaxanthin-containing condiment prepared by the above method.

In order to achieve the above objects, the present invention adopts the following technical solution:

A method for preparing an astaxanthin-containing condiment is provided, comprising the following steps:

(1) Wall-Breaking Treatment of *P. rhodozyma* Cells using water as a solvent to prepare a yeast suspension with a concentration of 10-100 g/L, adding glass beads with a particle size of 0.8-2.5 mm to make the content of the glass beads in the yeast suspension 100-500 g/L, then shaking to break walls at 120-170 rpm, and then removing the glass beads and precipitate to obtain a wall-broken yeast suspension;

(2) Preparation of Yeast Extract adding Angel yeast compound enzyme to the wall-broken yeast suspension, adjusting the pH to 5-8 for an enzymolysis reaction, then inactivating the enzyme, and performing solid-liquid separation to obtain a supernatant of an astaxanthin-containing yeast extract;

(3) Microencapsulation of Yeast Extract adding porous starch to water and heating for gelatinization to obtain a gelatinized starch solution, cooling the solution to a temperature of 50° C. to 60° C., then adding the supernatant of the astaxanthin-containing yeast extract to the gelatinized starch solution and stirring uniformly, then adding solid gelatin and shaking, and finally vacuum freeze-drying, breaking and sieving to obtain an astaxanthin-containing condiment.

The astaxanthin-containing condiment is microcapsule powder, whose core material is the astaxanthin-containing yeast extract, and whose wall material is the porous starch and gelatin.

The particle size of the glass beads described in step (1) is preferably 0.8-1.2 mm, more preferably 1 mm.

The content of the glass beads in the yeast suspension described in step (1) is preferably 300-500 g/L, more preferably 300 g/L.

The temperature for shaking to break walls described in step (1) is preferably 22° C. to 50° C., more preferably 22° C. to 40° C.

The rotational speed for shaking to break walls described in step (1) is preferably 150 rpm.

The time for shaking to break walls described in step (1) is preferably 6-48 h, more preferably 48 h.

The amount of the added Angel yeast compound enzyme described in step (2) is 0.5-3 wt % of the dry weight of the yeast in the wall-broken yeast suspension.

The temperature for the enzymolysis reaction described in step (2) is preferably 20° C. to 50° C., more preferably 40° C.

The time for the enzymolysis reaction described in step (2) is preferably 6-24 h.

The solid-liquid separation described in step (2) is preferably carried out by centrifugation.

The centrifugation is preferably carried out at a rotational speed of 8000-12000 rpm for 10-20 min.

The water described in step (3) is preferably distilled water.

The heating described in step (3) is preferably carried out with a boiling water bath.

The heating described in step (3) is preferably carried out for 10-20 min.

The amount of water described in step (3) is preferably determined according to the mass ratio of the porous starch to water of 25:75.

The mass ratio of the core material to the wall material described in step (3) is preferably 1:(1-10.6), more preferably 1:(1-6).

In the wall material described in step (3), the mass ratio of the porous starch to gelatin is preferably 1:(2-5), more preferably 2:5.

The temperature for the shaking in step (3) is preferably 20° C. to 50° C., more preferably 40° C.

The shaking described in step (3) is preferably carried out for 2-4 h.

The "vacuum freeze-drying" described in step (3) is preferably carried out for 24 h.

The present invention further provides an astaxanthin-containing condiment prepared by the above method.

Compared with the prior art, the present invention has the following advantages and beneficial effects:

(1) The present invention adopts glass beads with a certain particle size to break the wall of yeast through a relatively mild bead milling method; due to the prolonged wall-breaking time, astaxanthin can be directly emulsified and dispersed in water under the action of the shearing force of the glass beads, so that the concentration of astaxanthin can reach 1043.17 mg/L; in this way, the use of organic solvents and emulsifiers can be avoided, and thus the process operations can be reduced; besides, the problem of astaxanthin loss due to local temperature rise caused by high-speed bead milling can be solved.

(2) In the microencapsulation process of the present invention, the porous starch is pre-gelatinized first, and the ratio of the added porous starch is reduced, which can improve the water solubility of the microcapsule powder; first the porous starch is used to adsorb astaxanthin, and then gelatin is added to retain the color of astaxanthin and cover the smell of yeast; the composite wall material composed of the porous starch and gelatin can significantly improve the stability and water solubility of astaxanthin, which is beneficial to the application of the yeast extract in food; the astaxanthin-containing microcapsule powder prepared in this way has an encapsulation rate of 75.62% to 88.5%, and a drug-loading rate of 1.55-10.42 mg/g.

(3) The preparation method of the present invention is a green process with neither additions nor residues, has a short process flow and mild conditions, and is suitable for industrialization.

DETAILED DESCRIPTION OF THE EMBODIMENTS

The present invention will be further described below in detail with reference to examples, but the embodiments of the present invention are not limited thereto. Process parameters not specified can be determined with reference to conventional techniques.

Example 1

This example explored the conditions required for the use of glass beads to break the wall of *P. rhodozyma*

(1) Cell Wall Breaking of *P. rhodozyma* at Different Concentrations:

Adding *P. rhodozyma* (74220, purchased from ATCC, the same below) to 20 mL of water to obtain yeast suspensions with concentrations of 10 g/L, 20 g/L and 40 g/L (dry weight), adding glass beads with a particle size of 1 mm to the yeast suspensions to make the content of the glass beads in the yeast suspensions 200 g/L, and then shaking to break walls in a shaker at 22° C. at a stirring speed of 150 rpm for 6 h. After breaking the wall, centrifuging at 10000 rpm for 10 min, and then collecting the precipitate and supernatant. Extracting astaxanthin in the supernatant with acetone and back-extracting it with petroleum ether (refer to Gil-Hwan An. Applied and environmental microbiology, 1988, 55(1): 116-124 for extraction method), extracting the astaxanthin in the precipitate with acetone, and then using a spectrophotometer to detect the content of astaxanthin in the supernatant and precipitate. Using the amount of astaxanthin extracted by the acid-heat treatment method (refer to Ling-Yan Zhou, International Journal of Modern Biology and Medicine, 2015, 6(2):136-145 for the extraction method) as a control, i.e., regarding the amount of astaxanthin extracted by the acid-heat treatment method by default as the total amount of astaxanthin, and the extraction rate was the percentage of the amount of all the astaxanthin extracted by this method in the total amount of astaxanthin.

The results were as follows: The astaxanthin extraction rate of the yeast suspension with a yeast concentration of 10 g/L was 58.00%; the astaxanthin extraction rate of the yeast suspension with a yeast concentration of 20 g/L was 64.16%; and the astaxanthin extraction rate of the yeast suspension with a yeast concentration of 40 g/L was 33.13%.

(2) Effect of Further Increasing the Concentration of *P. rhodozyma* on the Solubility of Astaxanthin:

Adding *P. rhodozyma* to 20 mL of water to obtain yeast suspensions with concentrations of 20 g/L, 50 g/L and 100 g/L (dry weight), adding glass beads with a particle size of 1 mm to the yeast suspensions to make the content of the glass beads in the yeast suspensions 500 g/L, and then shaking to break walls in a shaker at 22° C. at a stirring speed of 150 rpm for 48 h. After breaking the wall, centrifuging at 10000 rpm for 10 min, and then collecting the precipitate and supernatant. Extracting astaxanthin in the supernatant with acetone and back-extracting it with petroleum ether, extracting the astaxanthin in the precipitate with acetone, and then using a spectrophotometer to detect the content of astaxanthin in the supernatant and precipitate. Using the amount of astaxanthin extracted by the acid-heat treatment method as a control, i.e., regarding the amount of astaxanthin extracted by the acid-heat treatment method by default as the total amount of astaxanthin for the calculation of the astaxanthin extraction rate.

The results were as follows: When the concentration of *P. rhodozyma* was 20 g/L and 50 g/L, respectively, the astaxanthin extraction rate of the yeast suspension could reach 100%, and the concentration of astaxanthin in the supernatant after the wall breaking was 459.57 mg/L and 843.06 mg/L, respectively; when the concentration of *P. rhodozyma* was 100 g/L, the astaxanthin extraction rate of the yeast suspension was 92.36%, and the concentration of astaxanthin in the supernatant after the wall breaking was 1043.17 mg/L.

(3) Cell Wall Breaking of *P. rhodozyma* at Different Temperatures:

Adding *P. rhodozyma* to 20 mL of water to obtain a yeast suspension with a concentration of 20 g/L (dry weight), adding glass beads with a particle size of 1 mm to the yeast suspension to make the content of the glass beads in the yeast suspension 200 g/L, and then shaking to break walls in a shaker at 22° C., 40° C. and 50° C. at a stirring speed of 150 rpm for 6 h. After breaking the wall, centrifuging at 10000 rpm for 10 min, and then collecting the precipitate and supernatant. Extracting astaxanthin in the supernatant with acetone and back-extracting it with petroleum ether, extracting the astaxanthin in the precipitate with acetone, and then using a spectrophotometer to detect the content of astaxanthin in the supernatant and precipitate. Using the amount of astaxanthin extracted by the acid-heat treatment method as a control, i.e., regarding the amount of astaxanthin extracted by the acid-heat treatment method by default as the total amount of astaxanthin for the calculation of the astaxanthin extraction rate.

The results were as follows: The astaxanthin extraction rate was 64.16% at 22° C., 67.83% at 40° C., and 36.01% at 50° C.

(4) Cell Wall Breaking of *P. rhodozyma* with Different Amount of Glass Beads Added:

Adding *P. rhodozyma* to 20 mL of water to obtain a yeast suspension with a concentration of 20 g/L (dry weight), adding glass beads with a particle size of 1 mm to the yeast suspension to make the content of the glass beads in the yeast suspension 100 g/L, 200 g/L and 300 g/L, respectively, and then shaking to break walls in a shaker at 22° C. at a stirring speed of 150 rpm for 6 h. After breaking the wall, centrifuging at 10000 rpm for 10 min, and then collecting the precipitate and supernatant. Extracting astaxanthin in the supernatant with acetone and back-extracting it with petroleum ether, extracting the astaxanthin in the precipitate with acetone, and then using a spectrophotometer to detect the content of astaxanthin in the supernatant and precipitate. Using the amount of astaxanthin extracted by the acid-heat treatment method as a control, i.e., regarding the amount of astaxanthin extracted by the acid-heat treatment method by default as the total amount of astaxanthin for the calculation of the astaxanthin extraction rate.

The results were as follows: The astaxanthin extraction rate was 47.66% when the amount of glass beads added was 100 g/L; the astaxanthin extraction rate was 64.16% when the amount of glass beads added was 200 g/L; and the astaxanthin extraction rate was 96.68% when the amount of glass beads added was 300 g/L.

(5) Cell Wall Breaking of *P. rhodozyma* Costing Different Wall-Breaking Time:

Adding *P. rhodozyma* to 20 mL of water to obtain a yeast suspension with a concentration of 20 g/L (dry weight), adding glass beads with a particle size of 1 mm to the yeast suspension to make the content of the glass beads in the yeast suspension 500 g/L, and then shaking to break walls in a shaker at 22° C. at a stirring speed of 150 rpm for 6 h, 24 h and 48 h, respectively. After breaking the wall, centrifuging at 10000 rpm for 10 min, and then collecting the precipitate and supernatant. Extracting astaxanthin in the supernatant with acetone and back-extracting it with petroleum ether, extracting the astaxanthin in the precipitate with acetone, and then using a spectrophotometer to detect the content of astaxanthin in the supernatant and precipitate. Using the amount of astaxanthin extracted by the acid-heat treatment method as a control, i.e., regarding the amount of astaxanthin extracted by the acid-heat treatment method by default as the total amount of astaxanthin for the calculation of the astaxanthin extraction rate.

The results were as follows: When the wall-breaking time was 6 h, 24 h and 48 h, respectively, the astaxanthin extraction rate could reach 100%, and the concentration of astaxanthin in the supernatant after the wall breaking was 93.72 mg/L, 306.43 mg/L and 459.57 mg/L, respectively.

(6) Wall Breaking of *P. rhodozyma* by Bead Milling:

Taking 1 ml of the yeast suspension with a concentration of 20 g/L in a matching high-strength 2 mL centrifuge tube, and adding 750 mg of glass beads thereto with a diameter of 0.1 mm. Shaking to mix the glass beads uniformly, and then placing the centrifuge tube in a Mini-Beadbeater-16 bead mill (115-230 V, 50-60 Hz) to break at 150 rpm for 8, 12 and 16 times, respectively, each time for 30 s.

The results were as follows: The astaxanthin extraction rate was 11.84% when breaking was carried out for 8 times, 45.07% when breaking was carried out for 12 times, and 72.13% when breaking was carried out for 16 times, but at this time the precipitate had been washed to colorless, indicating the loss of some pigment.

(7) Wall Breaking of *P. rhodozyma* by Enzymolysis:

Adding *P. rhodozyma* to 20 mL of water to obtain a yeast suspension with a concentration of 20 g/L (dry weight), in which the amount of the added Angel yeast compound enzyme was 0.5 wt %, 1 wt % and 3 wt % (dry weight), respectively; carrying out enzymolysis at 50° C. and 150 rpm for 4 h under dark conditions; and calculating the astaxanthin extraction rate after the reaction.

The results were as follows: When the amount of the added Angel yeast compound enzyme was 0.5 wt %, the astaxanthin extraction rate was 23.41%; when the amount of the added Angel yeast compound enzyme was 1 wt %, the astaxanthin extraction rate was 31.70%; and when the amount of the added Angel yeast compound enzyme was 3 wt %, the astaxanthin extraction rate was 42.83%.

Example 2

Angel yeast compound enzyme and glass beads both have the function of breaking yeast. Therefore, this example compared the methods for preparing yeast extract between enzymolysis after wall breaking and enzymolysis while wall breaking.

Experimental Group 1: Enzymolysis while Wall Breaking

Adding *P. rhodozyma* to 20 mL of water to obtain a yeast suspension with a concentration of 20 g/L (dry weight), adding glass beads with a particle size of 1 mm to the yeast suspension to make the content of the glass beads in the yeast suspension 300 g/L, then adding 0.5 wt %, 1 wt % and 3 wt % of Angel yeast compound enzyme, respectively, and then adjusting the pH of the yeast suspension to 8 and shaking for 30 h at 40° C. and 150 rpm, and finally centrifuging at 10000 rpm for 10 min and collecting the supernatant A.

Experimental Group 2: Enzymolysis after Wall Breaking

Adding *P. rhodozyma* to 20 mL of water to obtain a yeast suspension with a concentration of 20 g/L (dry weight), adding glass beads with a particle size of 1 mm to the yeast suspension to make the content of the glass beads in the yeast suspension 300 g/L, and then shaking to break walls in a shaker at 40° C. at a stirring speed of 150 rpm for 6 h. Filtering the glass beads and precipitate out to obtain a wall-broken yeast suspension. Adjusting the pH of the yeast suspension to 8, then adding the Angel yeast compound enzyme to 0.5 wt %, 1 wt % and 3 wt %, respectively, then continuing to carry out enzymolysis while shaking at 40° C. and 150 rpm for 24 h, and finally centrifuging at 10000 rpm for 10 min and collecting the supernatant B.

Determining the amino nitrogen yield of the supernatants A and B by formaldehyde titration (refer to Ri-Wang Li. Materials Science and Engineering C, 2017, 77:1035-1043 for the measurement method), taking a certain amount of supernatant and drying it to a constant weight at 105° C., and calculating the solid content (the solid content is the percentage of the mass of solids in the total mass of the original yeast).

The results were as follows: In experimental group 1, when the amount of the added cocktail enzyme (Angel Yeast, Co., Ltd) was 0.5 wt %, 1 wt % and 3 wt % (dry yeast weight), respectively, the corresponding amino nitrogen yield was 2.43%, 2.61% and 2.76%, respectively, and the solid content was 39.38%, 36.25% and 40.30%, respectively. In experimental group 2, when the amount of the added Angel yeast compound enzyme was 0.5 wt %, 1 wt % and 3 wt % (dry weight), respectively, the corresponding amino nitrogen yield was 3.51%, 3.58% and 3.65%, respectively, and the solid content was 48.63%, 49.22% and 47.18%, respectively, all higher than the amino nitrogen yields and solid contents obtained in experimental group 1. Therefore, a better wall-breaking effect could be obtained by adopting the technical solution of enzymolysis after wall breaking. In addition, since the amino nitrogen yield and solid content were not much different when different amounts of the compound enzyme were added, it was determined that the glass beads were removed after wall breaking, and then 0.5% Angel yeast compound enzyme was added to prepare the yeast extract.

Example 3

This example provided a method for preparing an astaxanthin-containing condiment and a control example for the microcapsule preparation.

(1) Adding *P. rhodozyma* to 20 mL of water to obtain a yeast suspension with a concentration of 20 g/L (dry weight), adding glass beads with a particle size of 1 mm to the yeast suspension to make the content of the glass beads in the yeast suspension 300 g/L, and then shaking to break walls in a shaker at 40° C. at a stirring speed of 150 rpm for 6 h. Filtering the glass beads and precipitate out to obtain a wall-broken yeast suspension. Adjusting the pH of the yeast suspension to 8, then adding the yeast compound enzyme to 0.5 wt %, then continuing to carry out enzymolysis while shaking at 40° C. and 150 rpm for 24 h, then boiling the yeast suspension for 3 min to inactivate the enzyme, and then centrifuging at 10000 rpm for 10 min to obtain the supernatant of the astaxanthin-containing yeast extract with an astaxanthin concentration of 93.72 mg/L.

(2) Adding porous starch to distilled water to a concentration of 25 wt %, gelatinizing by boiling water bath for 10 min to obtain a gelatinized starch solution, and then cooling to a temperature of 50° C. to 60° C. Adding the supernatant of the astaxanthin-containing yeast extract prepared in step (1) to the gelatinized starch solution and stirring to adsorb for 20 min, and then adding gelatin and shaking at different temperatures for a certain period of time for microencapsulation to form a stable emulsion.

Orthogonal experiment was used to design to explore the factors affecting the microencapsulation of pigment. The design factors and levels of the orthogonal experiment were as follows: Supernatant: 20 mL, 30 mL, and 40 mL; amount of gelatin added: 0.7 g, 1.0 g, and 1.5 g; amount of porous starch added: 0.5 g, 0.6 g, and 0.7 g; encapsulation temperature: 40° C., 45° C., and 50° C.; and encapsulation time: 2 h, 3 h, and 4 h.

This example selected the following optimal proportion: Supernatant (V, mL):gelatin (W, g):porous starch (W, g)=400:15:6 (core material (W, g):wall material (W, g)=3.95:21); the microencapsulation temperature was 40° C., and the microencapsulation time was 2 h. The encapsulation rate was calculated by detecting the total amount of pigment in the microcapsule powder and the amount of pigment on the surface (refer to Gomez-Estaca J. Food Hydrocolloids, 2016, 61:155-162). The amount of pigment on the surface was obtained by directly adding acetone for extraction. The total amount of pigment in the microcapsule powder was obtained as follows: dissolving the microcapsule powder in distilled water, shaking and then adding acetone thereto, mixing uniformly and then centrifuging, using petroleum ether to back-extract the pigment, and taking the upper layer of pigment-petroleum ether to measure the absorbance A with a spectrophotometer; if the pigment in the lower layer of acetone was not extracted completely, petroleum ether was added repeatedly until the organic solvent in the lower layer was colorless. Drug-loading rate refers to the amount of pigment contained in each gram of the microcapsule powder.

The solubility was determined by gravimetric method (refer to Talita A. Comunian. Food Research International, 2013, 52(1):373-379 for the determination method).

The encapsulation rate, drug-loading rate and solubility of the obtained astaxanthin-containing microcapsule powder were 88.5%, 1.55 mg/g and 79.13%, respectively. The content of amino nitrogen in the microcapsule powder was determined to be 1.35%.

(3) Adding porous starch and gelatin to the supernatant of the astaxanthin-containing yeast extract prepared in step (1) at the same time, stirring and adsorbing for 20 min, and then shaking at 40° C. for microencapsulation for 2 h; wherein the supernatant (V, mL):gelatin (W, g):porous starch (W, g)=400:15:6.

The results were as follows: After microencapsulation, the porous starch settled on the bottom and could not form a stable emulsion; the color distribution of the obtained microcapsule powder was nonuniform, and the encapsulation rate varied greatly. From the comparison of the results of steps (2) and (3), it can be seen that the order of adding the gelatinized porous starch first and then gelatin was more conducive to the microencapsulation of astaxanthin.

Example 4

This example provided a method for preparing microcapsules of different concentrations of astaxanthin.

Adding *P. rhodozyma* to 20 mL of water to obtain yeast suspensions with concentrations of 20 g/L, 50 g/L and 100 g/L (dry weight), adding glass beads with a particle size of 1 mm to the yeast suspensions to make the content of the glass beads in the yeast suspensions 500 g/L, and then shaking to break walls in a shaker at 22° C. at a stirring speed of 150 rpm for 48 h. Filtering the glass beads and precipitate out to obtain a wall-broken yeast suspension. Adjusting the pH of the yeast suspension to 8, then adding the yeast compound enzyme to 0.5%, then continuing to carry out enzymolysis while shaking at 40° C. and 150 rpm for 24 h, then boiling the yeast suspension for 3 min to inactivate the enzyme, and then centrifuging at 10000 rpm for 10 min to obtain a supernatant of an astaxanthin-containing yeast extract. The supernatant was encapsulated according to the following microencapsulation conditions determined by the orthogonal experiment: supernatant (V, mL):gelatin (W, g):porous starch (W, g)=400:15:6, the microencapsulation temperature was 40° C., and the microencapsulation time was 2 h.

The results were as follows: When the concentration of yeast was 20 g/L, the encapsulation rate and drug-loading rate of astaxanthin were 87.8% and 3.45 mg/g, respectively; when the concentration of yeast was 50 g/L, the encapsulation rate and drug-loading rate of astaxanthin were 78.69% and 6.79 mg/g, respectively; when the concentration of yeast was 100 g/L, the encapsulation rate and drug-loading rate of astaxanthin were 75.62% and 10.42 mg/g, respectively. Refer to Example 3 for the detection methods of the encapsulation rate and drug-loading rate.

The above examples are preferred embodiments of the present invention, but the embodiments of the present invention are not limited thereto, and any other alterations, modifications, replacements, combinations and simplifications made without departing from the spirit and principle of the present invention should all be equivalent substitutions and included in the scope of protection of the present invention.

The invention claimed is:

1. A method for preparing an astaxanthin-containing condiment, characterized in that: the method comprises the following steps:
   (1) wall-breaking treatment of *Phaffia rhodozyma* cells using water as a solvent to prepare a yeast suspension with a concentration of 10-100 g/L, adding glass beads with a particle size of 0.8-2.5 mm to make the content of the glass beads in the yeast suspension 100-500 g/L, then shaking to break walls at 120-170 rpm, and then removing the glass beads and precipitate to obtain a wall-broken yeast suspension;
   (2) preparation of yeast extract
   adding compound enzyme to the wall-broken yeast suspension, adjusting the pH to 5-8 for an enzymolysis reaction, then inactivating the enzyme, and performing solid-liquid separation to obtain a supernatant of an astaxanthin-containing yeast extract;
   (3) microencapsulation of yeast extract
   adding porous starch to water and heating for gelatinization to obtain a gelatinized starch solution, cooling the solution to a temperature of 50° C. to 60° C., then adding the supernatant of the astaxanthin-containing yeast extract to the gelatinized starch solution and stirring uniformly, then adding solid gelatin and shaking, and finally vacuum freeze-drying, breaking and sieving to obtain an astaxanthin-containing condiment;
   the astaxanthin-containing condiment is microcapsule powder, whose core material is the astaxanthin-containing yeast extract, and whose wall material is the porous starch and gelatin.

2. The method for preparing the astaxanthin-containing condiment according to claim 1, characterized in that:
   the particle size of the glass beads described in step (1) is 0.8-1.2 mm; and
   the content of the glass beads in the yeast suspension described in step (1) is 300-500 g/L.

3. The method for preparing the astaxanthin-containing condiment according to claim 1, characterized in that: the conditions for the "shaking to break walls" described in step (1) are as follows: the temperature is 22° C. to 50° C., the rotational speed is 150 rpm, and the wall-breaking time is 6-48 h.

4. The method for preparing the astaxanthin-containing condiment according to claim 1, characterized in that: the amount of the added Angel yeast compound enzyme described in step (2) is 0.5-3 wt % of the dry weight of the yeast in the wall-broken yeast suspension.

5. The method for preparing the astaxanthin-containing condiment according to claim 1, characterized in that: the enzymolysis reaction described in step (2) is carried out at 20° C. to 50° C. for 6-24 h.

6. The method for preparing the astaxanthin-containing condiment according to claim 1, characterized in that:
   the solid-liquid separation described in step (2) is carried out by centrifugation;
   the water described in step (3) is distilled water; and
   the "heating" described in step (3) is carried out with a boiling water bath.

7. The method for preparing the astaxanthin-containing condiment according to claim 1, characterized in that:
   the amount of water described in step (3) is determined according to the mass ratio of the porous starch to water of 25:75.

8. The method for preparing the astaxanthin-containing condiment according to claim 1, characterized in that:
   the mass ratio of the core material to the wall material described in step (3) is 1:(1-10.6); and
   in the wall material described in step (3), the mass ratio of the porous starch to gelatin is 1:(2-5).

9. The method for preparing the astaxanthin-containing condiment according to claim 1, characterized in that:
   the "shaking" described in step (3) is carried out at a temperature of 20° C. to 50° C.;
   the "shaking" described in step (3) is carried out for 2-4 h; and
   the "vacuum freeze-drying" described in step (3) is carried out for 24 h.

* * * * *